US012076213B2

(12) United States Patent
Waite et al.

(10) Patent No.: US 12,076,213 B2
(45) Date of Patent: Sep. 3, 2024

(54) MULTILAYERED PRIMARY CONTACT WOUND DRESSING

(71) Applicants: SYSTAGENIX WOUND MANAGEMENT, LIMITED, West Sussex (GB); KCI USA, INC., San Antonio, TX (US)

(72) Inventors: Alexander Waite, Cowling (GB); Katherine A. Bourdillon, Leeds (GB)

(73) Assignee: KCI USA, Inc., San Antonio, TX (US)

( * ) Notice: Subject to any disclaimer, the term of this patent is extended or adjusted under 35 U.S.C. 154(b) by 966 days.

(21) Appl. No.: 16/762,234

(22) PCT Filed: Nov. 7, 2018

(86) PCT No.: PCT/US2018/059620
§ 371 (c)(1),
(2) Date: May 7, 2020

(87) PCT Pub. No.: WO2019/094466
PCT Pub. Date: May 16, 2019

(65) Prior Publication Data
US 2020/0345557 A1    Nov. 5, 2020

Related U.S. Application Data

(60) Provisional application No. 62/584,010, filed on Nov. 9, 2017.

(51) Int. Cl.
| | |
|---|---|
| *A61F 13/01* | (2024.01) |
| *A61F 13/00* | (2024.01) |
| *A61F 13/05* | (2024.01) |
| *A61L 15/22* | (2006.01) |
| *A61L 15/32* | (2006.01) |
| *A61L 15/42* | (2006.01) |
| *A61L 15/64* | (2006.01) |

(52) U.S. Cl.
CPC .. *A61F 13/01029* (2024.01); *A61F 13/00063* (2013.01); *A61F 13/01012* (2024.01); *A61F 13/05* (2024.01); *A61L 15/225* (2013.01); *A61L 15/325* (2013.01); *A61L 15/425* (2013.01); *A61L 15/64* (2013.01); *A61F 2013/00221* (2013.01); *A61L 2300/104* (2013.01); *A61L 2300/106* (2013.01); *A61L 2300/206* (2013.01); *A61L 2300/21* (2013.01); *A61L 2300/232* (2013.01); *A61L 2300/402* (2013.01); *A61L 2300/404* (2013.01); *A61L 2300/41* (2013.01); *A61L 2430/34* (2013.01)

(58) Field of Classification Search
None
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

(Continued)

*Primary Examiner* — Robert A Wax
*Assistant Examiner* — Quanglong N Truong

(57) ABSTRACT

The wound dressing described herein can be used as a contact layer dressing. The wound dressing can be positioned between a wound bed and a secondary dressing. The wound dressing can include a layered construction. Each of the layers can include a bioresorbable sponge enclosed within a collagen-based film. The wound dressing can include a plurality of fluid channels that enable fluid flow from the wound bed toward the environment-face side of the wound dressing.

22 Claims, 4 Drawing Sheets

(56) References Cited

U.S. PATENT DOCUMENTS

| | | |
|---|---|---|
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,700,476 A * | 12/1997 | Rosenthal ............... A61L 15/32 514/777 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2015/0174291 A1 | 6/2015 | Zimnitsky et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 562 862 A1 | 9/1993 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2008/091521 A2 | 7/2008 |
| WO | WO-2009/097534 A1 | 8/2009 |

OTHER PUBLICATIONS

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

(56) References Cited

OTHER PUBLICATIONS

Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report & Written Opinion in International Application No. PCT/US2018/059620, mailed on Feb. 28, 2019.

* cited by examiner

MULTILAYERED PRIMARY CONTACT WOUND DRESSING

CROSS-REFERENCE TO RELATED APPLICATIONS

The present application is a U.S. National Phase Application under 35 U.S.C. § 371 of International Patent Application No. PCT/US2018/059620, filed on Nov. 7, 2018, which claims the benefit, under 35 USC § 119(e), of the filing of U.S. Provisional Patent Application 62/584,010, titled "MULTILAYERED PRIMARY CONTACT WOUND DRESSING," filed Nov. 9, 2017. Each foregoing application is incorporated herein by reference for all purposes.

BACKGROUND OF THE DISCLOSURE

When wound dressings are used for extended periods of time, tissue can ingress into the wound dressing. The ingressed tissue can adhere the wound dressing to the wound bed, making it difficult and painful to remove the wound dressing. To combat tissue ingress, wound dressings can be replaced regularly before the tissue has the opportunity to ingress into the wound dressing. However, frequent changing of the wound dressing can disrupt the tissue of the wound bed and also lead to patient discomfort.

SUMMARY OF THE DISCLOSURE

According to an aspect of the disclosure, a wound contact dressing can include a first bioresorbable sponge. The first bioresorbable sponge can be configured to degrade over a first predetermined amount of time. The first bioresorbable sponge can include a first plurality of fluid channels through the first bioresorbable sponge. The wound contact dressing can include a first collagen-based film substantially covering a first face of the first bioresorbable sponge. The first collagen-based film can line an internal wall of each of the first plurality of fluid channels. The wound contact dressing can include a second bioresorbable sponge. The second bioresorbable sponge can be configured to degrade over a second predetermined amount of time. The second bioresorbable sponge can include a second plurality of fluid channels through the second bioresorbable sponge. The wound contact dressing can include a second collagen-based film between the first bioresorbable sponge and the second bioresorbable sponge. The second collagen-based film can substantially cover a first face of the second bioresorbable sponge and line an internal wall of each of the second plurality of fluid channels. The wound contact dressing can include a third collagen-based film substantially covering a second face of the second bioresorbable sponge.

In some implementations, the first bioresorbable sponge and the second bioresorbable sponge can include freeze-dried collagen. The first bioresorbable sponge and the second bioresorbable sponge can include about 55% collagen and about 45% oxidized regenerated cellulose by weight. The first bioresorbable sponge and the second bioresorbable sponge can include about 55% collagen, about 44% oxidized regenerated cellulose (ORC), and about 1% silver-ORC by weight.

In some implementations, the second collagen-based film substantially covers a second face of the first bioresorbable sponge. The first collagen-based film, the second collagen-based film, and the third collagen-based film can include at least one of a high-density collagen film or a cross-linked collagen film.

In some implementations, each of the first plurality of fluid channels and the second plurality of channels are configured to enable fluid flow from a wound site to a secondary dressing.

In some implementations, the first predetermined amount of time is different than the second predetermined amount of time. The first bioresorbable sponge can include a higher collagen density than the second bioresorbable sponge. The first bioresorbable sponge can be a wound-facing layer and the second bioresorbable sponge is an environment-facing layer.

In some implementations, the first bioresorbable sponge can include an antimicrobial agent and the second bioresorbable sponge does not comprise the antimicrobial agent. In some implementations, the second bioresorbable sponge can include an anti-inflammatory agent. In some implementations, the first bioresorbable sponge and the second bioresorbable sponge can include at least one of an anti-oxidant or an analgesic. The first bioresorbable sponge can include at least one of polyhexamethylene biguanide, citric acid, silver, silver-ORC, or iodine.

In some implementations, the first collagen-based film, the second collagen-based film, and the third collagen-based film can include a plasticizer. In some implementations, the first collagen-based film, the second collagen-based film, and the third collagen-based film can degrade over a third predetermined amount of time. The third predetermined amount of time can be greater than the first predetermined amount of time and the second predetermined amount of time.

In some implementations, the wound contact dressing can include a non-resorbable backing layer that can be coupled with the third collagen-based film.

According to an aspect of the disclosure, a wound dressing can include a backing layer that has a first environment-facing side and a first wound-facing side. The backing layer can be liquid impermeable and vapor permeable. The wound dressing can include a first collagen-based sponge layer that can be coupled with the backing layer. The first collagen-based sponge layer can include a first plurality of fluid channels. The wound dressing can include a first film layer substantially covering a wound-facing side of the first collagen-based sponge layer. The wound dressing can include a second collagen-based sponge layer coupled with the first film layer. The second collagen-based sponge layer can include a second plurality of fluid channels. The wound dressing can include a second film layer substantially covering a wound-facing side of the second collagen-based sponge layer.

In some implementations, the first film layer substantially covers an inner wall of each of the first plurality of fluid channels and the second film layer substantially covers an inner wall of each of the second plurality of fluid channels. The first film layer and the second film layer can include at least one of a high-density collagen film or a cross-linked collagen film.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Figure 1:
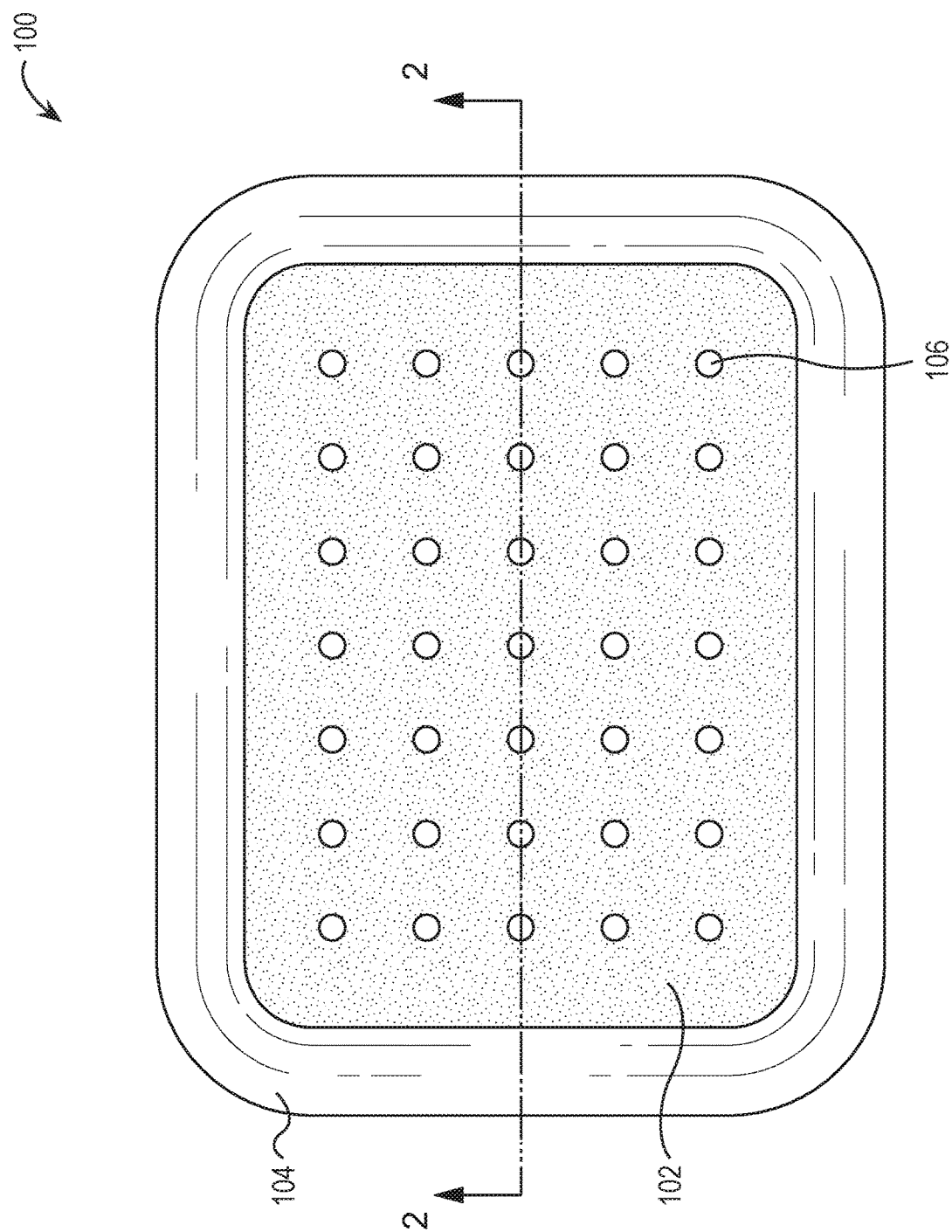
FIG. 1 illustrates a top view of an example wound dressing.

In the drawings, like reference characters generally refer to like features, functionally similar elements, and/or structurally similar elements throughout the various drawings. The drawings are not necessarily to scale, emphasis instead being placed upon illustrating the principles of the teachings. The drawings are not intended to limit the scope of the present teachings in any way.

The disclosure describes a wound dressing. The wound dressing can be a bioresorbable primary contact layer dressing designed to sit between the wound bed and a secondary dressing or other material. The wound dressing can be a multi-layered dressing that can include one or more layers of a collagen-based film and a bioresorbable material, such as collagen. The wound dressing can also include a plurality of fluid channels that can pass through the wound dressing and enable exudate to flow through the channels and away from the wound bed.

Adhesion of a secondary dressing can cause patient discomfort. Tissue ingress into the secondary dressing can also cause patient discomfort. To reduce tissue ingress, dressings can often be changed regularly before tissue has the opportunity to ingress into the dressing. The wound dressing of the present disclosure can reduce wound bed adhesion of the wound dressing itself or a secondary dressing to the wound bed. The wound dressing of the present disclosure can also limit tissue ingress into the secondary dressing. The present wound dressing can limit adhesion and tissue ingress by providing a bioresorbable matrix between the wound bed and the secondary dressing. The bioresorbable wound dressing provides a spacing between the secondary dressing and is absorbed by the patient's body over time. Because the patient's body absorbs the wound dressing, the wound dressing does not need to be removed. This can reduce tissue disruption and patient discomfort.

FIG. 1 illustrates a top view of an example wound dressing 100. The wound dressing 100 can be a bioresorbable primary contact layer dressing that is configured for extended wear time. The wound dressing 100 includes multiple layers of bioresorbable sponge 102 that are each encloses in a film 104. In some implementations, the film 104 is a collagen-based film. The wound dressing 100 includes a plurality of fluid channels 106 that run through the layers of the wound dressing 100.

The wound dressing 100 can be a bioresorbable primary contact layer dressing configured to sit between the wound bed and a secondary dressing. The wound dressing 100 can provide protection against tissue ingress into the secondary dressing. In some implementations, the bioresorbable nature of the wound dressing 100 enables the wound dressing 100 to be left in place until substantially dissolved. Once dissolved, a new wound dressing 100 can be applied to the wound bed.

The bioresorbable sponge 102 included in wound dressing 100 can include a freeze-dried collagen. In some implementations, the bioresorbable sponge 102 can include oxidized regenerated cellulose (ORC). The bioresorbable sponge 102 can include between about 30% and about 70%, between about 40% and about 60%, or between about 50% collagen by weight. In some implementations, the bioresorbable sponge 102 can include between about 30% and about 70%, between about 40% and about 60%, or between about 40% and about 50% ORC by weight. In some implementations, the bioresorbable sponge 102 can include about 55% collagen by weight and about 45% ORC by weight.

In some implementations, the bioresorbable sponge 102 can include an antimicrobial agent. Example antimicrobial agents can include polyhexamethylene biguanide (PHMB), citric acid, silver, iodine, silver-ORC, or any combination thereof. In some implementations, the bioresorbable sponge 102 can include between about 1% and about 10%, between about 1% and about 5%, or between about 1% and about 3% of antimicrobial material by weight. In some implementations, the bioresorbable sponge 102 can include chitosan or gelatine. The bioresorbable sponge 102 can include one or more types of agents. The types of agents can include one or more of an anti-inflammatory agent, anti-oxidant agent, analgesic agent, or any combination thereof. In some implementations, different bioresorbable sponges 102 can include different agents or different levels of agents. For example, only a portion of the bioresorbable sponges 102 may contain an antimicrobial (e.g., the bioresorbable sponge 102 from every other layer 108) to reduce the chance of causing cytotoxicity.

The wound dressing 100 can include multiple layers of film 104. Each bioresorbable sponge 102 can be enclosed in a layer of the film 104. The film 104 can substantially cover each of bioresorbable sponges' faces. For example, the film 104 can form a barrier between the bioresorbable sponges 102 and the external environment. The film 104 can protect the bioresorbable sponges 102 from enzymatic degradation. In some implementations, the film 104 can withstand enzymatic degradation for a longer time period when compared to the bioresorbable sponge 102. In some implementations, as the enzymes break down the collagen of the wound dressing 100, the enzymes are no longer available to break down the wound bed. The film 104 can cover the internal walls defined by the fluid channels 106 that pass through the layers of the wound dressing 100. The film 104 can be a high-density collagen film. In some implementations, the film 104 can be a cross-linked collagen film. In some implementations, the film 104 is between about 10 μm and about 300 μm, between about 100 μm and about 300 μm, or between about 200 μm and about 300 μm.

The wound dressing 100 can include a plurality of fluid channels 106. The fluid channels 106 can pass through the structures of the wound dressing 100 and are illustrated further in FIGS. 2 and 3. The fluid channels 106 enable wound exudate to flow through the wound dressing 100 and can reduce the contact of the wound dressing 100 with the wound bed. In some implementations, the fluid channels 106 can have a diameter between about 0.5 mm and about 5 mm, between about 0.5 mm and about 4 mm, between about 1 mm and about 3 mm, or between about 1 mm and about 2 mm. In some implementations, neighboring fluid channels 106 can be separated by between about 1 mm and about 15 mm, between about 5 mm and about 15 mm, or between about 10 and about 15 mm.

Figure 2:
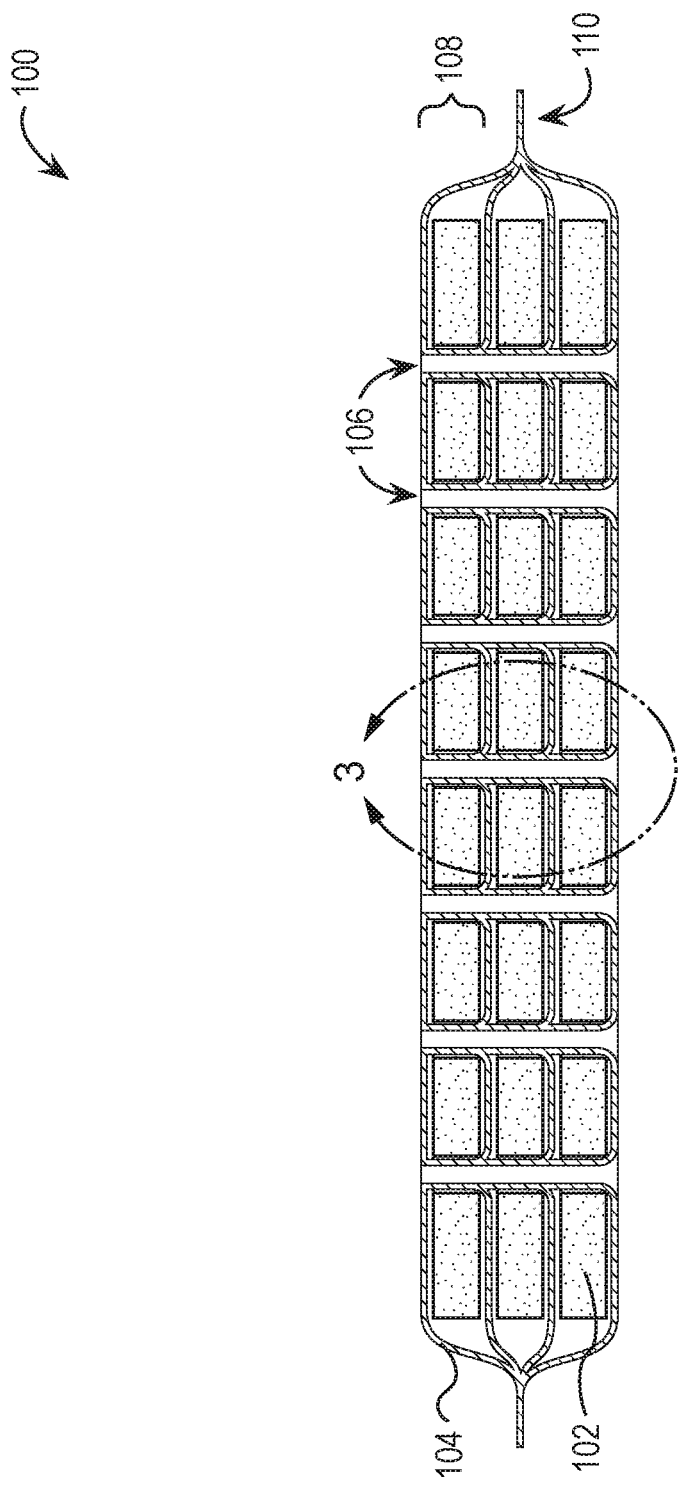
FIG. 2 illustrates a cross-sectional view of the example wound dressing illustrated in FIG. 1.

FIG. 2 illustrates a cross-sectional view of the example wound dressing 100 illustrated in FIG. 1. FIG. 2 illustrates the cross-section of the wound dressing 100 made at the cut line A, illustrated in FIG. 1. The cut line A passes through a row of fluid channels 106.

As illustrated, the wound dressing 100 includes three layers 108. Each of the layers 108 include at least one bioresorbable sponge 102 and at least one layer of film 104.

Each of the layers 108 are configured to degrade over a predetermined amount of time. The wound dressing 100 can degrade over about 7 days to 21 days. In some implementations, the wound dressing 100 can include a layered pattern that alternates between layers of bioresorbable sponge 102 and film 104. In some implementations, each of bioresorbable sponges 102 can degrade over substantially the same length of time. In some implementations, each of the bioresorbable sponges 102 can be configured to degrade at a different rate. For example, the bioresorbable sponges 102 can degrade over a length of time between about 1 and about 14 days or between about 7 and 14 days.

The wound dressing 100 can have an alternating layer construction. For example, each layer 108 can include a bioresorbable sponge 102 and at least one layer of film 104. The layers 108 can be stacked to form the wound dressing 100. In some implementations, the wound dressing 100 can include between about 1 and about 10 layers 108, between about 1 and about 8 layers 108, between about 1 and about 6 layers 108, or between about 1 and about 4 layers 108.

In some implementations, each of the layers 108 can include about 1, 2, 3, 4, or 5 bioresorbable sponges 102 that are not separated by a layer of film 104. For example, each of the layers 108 can include a different number of bioresorbable sponges 102 such that the layers 108 degrade a different rates (e.g., a layer 108 with relatively more bioresorbable sponges 102 can take relatively longer to degrade). Each layer 108 can be between about 1 mm and about 10 mm thick, between about 3 mm and about 8 mm thick, or between about 3 mm and about 6 mm thick.

The perimeters of the multiple layers 108 (e.g., the portions of the film 104 that overhang the bioresorbable sponges 102) can be fused together to form a laminated edge 110. The layers 108 can be fused together at the laminated edge 110 by applying pressure and heat to the perimeters of the layers 108. In some implementations, a bonding agent can be used to fuse the layers 108 together to form the laminated edge 110.

Figure 3:
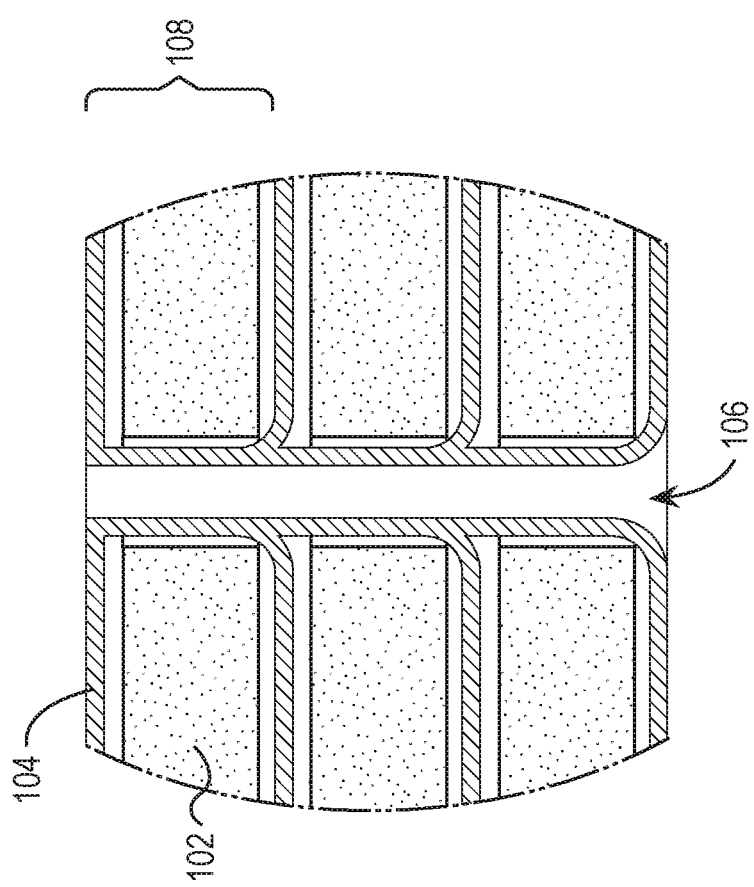
FIG. 3 illustrates an enlarged view of a fluid channel illustrated in FIG. 2.

FIG. 3 illustrates an enlarged view of a fluid channel 106 illustrated in FIG. 2. The fluid channel 106 can pass through each of the layers 108 and enable fluid flow from the wound facing side of the device toward the environment facing side of the wound dressing 100. For example, each layer 108 can include a portion of the fluid channels' total length. The portions of the fluid channel 106 from each of the layers 108 are aligned to form the fluid channel 106 through the wound dressing 100. The film 104 can line the internal wall or face of the fluid channels 106.

In some implementations, the fluid channels 106 are formed by perforating the wound dressing 100 with a cutting die that punctures the wound dressing 100 at predetermined locations. The cutting die can stretch portions of the film 104 into the lumen of the fluid channel 106. The film 104 can stick to, and line, the internal walls of the fluid channels 106. The stretch of the film 104 can be controlled by the level of plasticizer included in the film 104. The plasticizer can be glycerol. The plasticizer can be included in the slurry mixture used to form the film 104 at a concentration of between about 0.1% to about 1%, between about 0.1% and about 0.8%, or between about 0.1% and about 0.5%.

Figure 4:
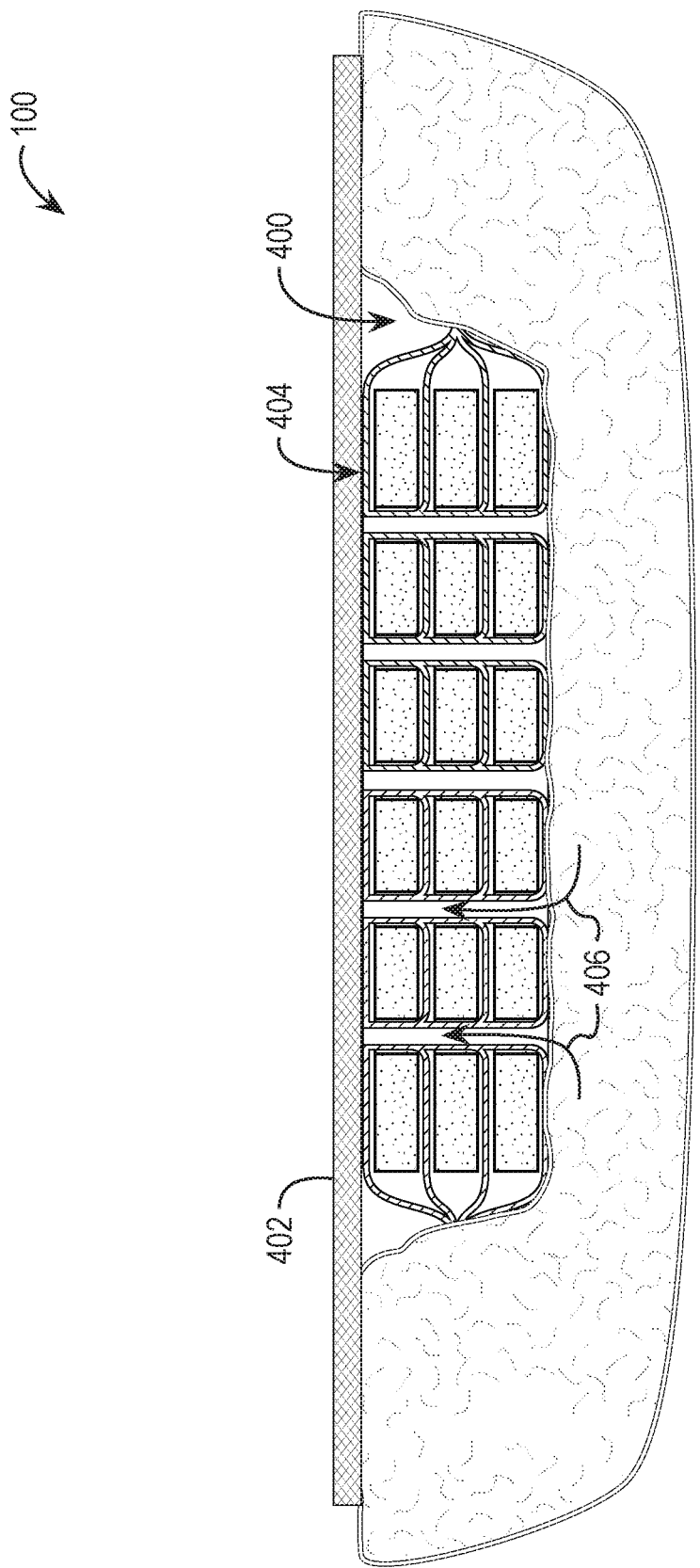
FIG. 4 illustrates a cross-sectional view of a wound dressing placed in a wound bed.

FIG. 4 illustrates a cross-sectional view of a wound dressing 100 placed in a wound bed 400. The wound dressing 100 includes a backing layer 402 coupled with an environment-facing side 404. Fluid flow 406 can pass from the wound bed 400 towards the backing layer 402. In some implementations, the backing layer 402 can be a secondary dressing.

The backing layer 402 can be a liquid impermeable layer. The backing layer 402 can be vapor permeable. The backing layer 402 can be impermeable to wound exudate or other wound fluids. The backing layer 402 can provide a barrier to the passage of microorganisms, bacteria, and other contaminants through the wound dressing 100 to the wound bed 400.

In some implementations, the backing layer 402 is a component of the wound dressing 100. The backing layer 402 can be a thin layer of polyurethane film. For example, the backing layer 402 can include the polyurethane film ESTANE 5714F. The backing layer 402 can include poly alkoxyalkyl acrylates and methacrylates. In some implementations, the backing layer 402 includes a continuous layer of a high-density blocked polyurethane foam that is predominantly closed-cell. The backing layer 402 can have a thickness between about 10 μm and about 100 μm, between about 25 μm and about 75 μm, or between about 50 μm and about 75 μm.

The backing layer 402 can extend beyond the perimeter of the wound dressing 100. The backing layer's wound-facing side can be coated with an acrylic or other adhesive. The adhesive can couple with the patient's skin or other surface during wear time. In some implementations, the environment-facing side 404 can include a tacky adhesive that couples with the backing layer 402 when the backing layer 402 is pressed against the wound dressing 100. The adhesive applied to the environment-facing side 404 can be moisture vapor transmitting. The application of the adhesive can be patterned to enable the passage of water vapor through the backing layer 402. The adhesive may include a continuous moisture vapor transmitting, pressure-sensitive adhesive layer of the type used for island-type wound dressings (e.g., a polyurethane-based pressure sensitive adhesive). One example of an adhesive which can be used is a pressure-sensitive adhesive based on acrylate ester copolymers, polyvinyl ethyl ether, and polyurethane.

In some implementations, the wound dressing 100 described herein can be used in negative-pressure wound therapy (NPWT). For example, and also referring to FIG. 4, a vacuum can be used to generate a negative (or reduced) pressure in the space between the wound bed 400 and the backing layer 402. The wound dressing 100 can ensure that as the negative pressure is applied to the wound, the backing layer 402 does not come into contact with the wound bed 400.

In some implementations, the wound dressing 100 described herein can be a component of a kit. The kit can include any wound dressing described herein and instructions for use. The kit can include instructions for treating a wound in a subject in need thereof. The kit can include antiseptic wipes, ointment, adhesive tape, tweezers, scissors, or other devices or components for the placement or removal of the wound dressing from a subject.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations or implementations.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Where technical features in the drawings, detailed description, or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A wound contact dressing comprising:
   a first bioresorbable sponge configured to degrade over a first predetermined amount of time, the first bioresorbable sponge comprises a first plurality of fluid channels that cut through the first bioresorbable sponge;
   a first collagen-based film substantially covering a first face of the first bioresorbable sponge and lining an internal wall of each of the first plurality of fluid channels;
   a second bioresorbable sponge configured to degrade over a second predetermined amount of time, the second bioresorbable sponge comprises a second plurality of fluid channels that cut through the second bioresorbable sponge;
   a second collagen-based film between the first bioresorbable sponge and the second bioresorbable sponge, the second collagen-based film substantially covering a first face of the second bioresorbable sponge and lining an internal wall of each of the second plurality of fluid channels; and
   a third collagen-based film substantially covering a second face of the second bioresorbable sponge.

2. The wound contact dressing of claim 1, wherein the first bioresorbable sponge and the second bioresorbable sponge comprise freeze-dried collagen.

3. The wound contact dressing of claim 1, wherein the first bioresorbable sponge and the second bioresorbable sponge comprise about 55% collagen and about 45% oxidized regenerated cellulose by weight.

4. The wound contact dressing of claim 1, wherein the first bioresorbable sponge and the second bioresorbable sponge comprises about 55% collagen, about 44% oxidized regenerated cellulose, and about 1% silver-ORC by weight.

5. The wound contact dressing of claim 1, wherein the second collagen-based film substantially covers a second face of the first bioresorbable sponge.

6. The wound contact dressing of claim 1, wherein the first collagen-based film, the second collagen-based film, and the third collagen-based film comprise at least one of a high-density collagen film or a cross-linked collagen film.

7. The wound contact dressing of claim 1, wherein each of the first plurality of fluid channels and the second plurality of channels are configured to enable fluid flow from a wound site to a secondary dressing.

8. The wound contact dressing of claim 1, wherein the first predetermined amount of time is different than the second predetermined amount of time.

9. The wound contact dressing of claim 1, wherein the first bioresorbable sponge comprises a higher collagen density than the second bioresorbable sponge.

10. The wound contact dressing of claim 1, wherein the first bioresorbable sponge is a wound facing layer and the second bioresorbable sponge is an environment facing layer.

11. The wound contact dressing of claim 10, wherein the first bioresorbable sponge comprises an antimicrobial agent and the second bioresorbable sponge does not comprise the antimicrobial agent.

12. The wound contact dressing of claim 11, wherein the second bioresorbable sponge comprises an anti-inflammatory agent.

13. The wound contact dressing of claim 1, wherein the first bioresorbable sponge and the second bioresorbable sponge comprise at least one of an anti-oxidant or an analgesic.

14. The wound contact dressing of claim 1, wherein the first bioresorbable sponge comprises at least one of polyhexamethylene biguanide, citric acid, silver, silver-ORC, or iodine.

15. The wound contact dressing of claim 1, wherein the first collagen-based film, the second collagen-based film, and the third collagen-based film comprise a plasticizer.

16. The wound contact dressing of claim 1, wherein the first collagen-based film, the second collagen-based film, and the third collagen-based film degrade over a third predetermined amount of time, wherein the third predetermined amount of time is greater than the first predetermined amount of time and the second predetermined amount of time.

17. The wound contact dressing of claim 1, further comprising:
   a non-resorbable backing layer coupled with the third collagen-based film.

18. The wound contact dressing of claim 1, wherein the first bioresorbable sponge is enclosed by the first collagen-based film and the second collagen-based film, and wherein the second bioresorbable sponge is enclosed by the second collagen-based film and the third collagen-based film.

19. The wound contact dressing of claim 18, wherein the first collagen-based film, the second collagen-based film, and the third collagen-based film form a barrier between both the first bioresorbable sponge and the second bioresorbable sponge and the external environment.

20. The wound contact dressing of claim 18, wherein the first collagen-based film, the second collagen-based film, and the third collagen-based film are fused together at a laminated edge.

21. The wound contact dressing of claim 1, wherein the first plurality of fluid channels are aligned with the second plurality of fluid channels.

22. The wound contact dressing of claim 1, wherein the first bioresorbable sponge and the second bioresorbable sponge each comprise a porous structure, and wherein the first plurality of fluid channels perforate the porous structure of the first bioresorbable sponge and the second plurality of fluid channels perforate the porous structure of the second bioresorbable sponge.

* * * * *